United States Patent [19]
Smith

[11] Patent Number: 6,082,485
[45] Date of Patent: Jul. 4, 2000

[54] ADJUSTABLE EARPLUG

[76] Inventor: Eric B. Smith, 1700 Church St., Suite 1244, San Francisco, Calif. 94131

[21] Appl. No.: 09/370,598

[22] Filed: Aug. 10, 1999

[51] Int. Cl.⁷ ........................................................ A61B 7/02
[52] U.S. Cl. ............................................ 181/135; 128/868
[58] Field of Search .................................... 181/135, 129, 181/130, 131, 132, 134, 137; 128/864, 868

[56] References Cited

U.S. PATENT DOCUMENTS

| | | | |
|---|---|---|---|
| 3,702,123 | 11/1972 | Macken | 181/135 |
| 3,934,100 | 1/1976 | Harada | 181/135 |
| 5,332,871 | 7/1994 | Carrigan | 181/135 |

*Primary Examiner*—Khanh Dang
*Attorney, Agent, or Firm*—Townsend and Townsend and Crew LLP

[57] ABSTRACT

An earplug has a rotationally adjustable gating mechanism for adjustable attenuation of treble sounds. The plug includes a conventional earplug foam body for conforming to and wedging in the ear canal. This earplug foam body includes at least a partial aperture axially of the plug leading from the exterior of the ear canal toward the interior of the ear canal with its hearing sense. A two-part counter rotating gating member fits to the aperture of the earplug. One part of the two part counter rotating gating member has a conical through aperture concentric to the earplug and ear canal. This conical through aperture is partially obstructed by an eccentrically mounted gate. The remaining part of the two part counter rotating gating member defines a rotating cover over the conical aperture and defines at least one and preferably a plurality of sound apertures enabling sound to pass from the exterior of the earplug into the conical aperture. These sound apertures are eccentrically mounted with respect to the conical aperture and the relative rotation to come into and out of registry with the eccentrically mounted gate. The two-part counter rotating gating member has an interference fit into the aperture of the earplug. When the earplug foam body is wedged into the ear, upon relative rotation of the cover with respect to the seat, the sound apertures rotate into and out of registry with the gate. There results an earplug assembly, which can selectively attenuate the treble sounds causing ear discomfort.

6 Claims, 3 Drawing Sheets

ADJUSTABLE EARPLUG

This invention relates to an adjustable earplug. More particularly, a conventional foam earplug is provided with at least a partial sound channel extending from the exterior of the ear into the ear canal. Into the sound channel, a rotating two-part plug is inserted. One member of the rotating two-part plug includes an eccentric gating baffle; the other member of the rotating two-part plug includes eccentrically mounted sound apertures. When the parts are relatively rotated and the sound apertures come into and out of registry with the gate of the gating member treble sounds are attenuated

BACKGROUND OF THE INVENTION

Conventional foam earplugs are known. These plugs have a continuum of foam, are cylindrical or slightly tapered and are larger that the acoustical canal of the ear. By wedging the plugs into the ear canal, the exterior surface of the plugs conforms to the ear canal and the central portion of the plug inhibits the penetration of at least treble sounds to the car canal.

Regarding so-called "treble sounds," it is the acoustical "highs" or treble sounds that both make listening in a high noise environment painful to the ear and permanently damaging to hearing sense.

In Carrigan U.S. Pat. No. 5,332871 issued Jul. 26, 1994 entitled Sliding Valve Ear Plug an earplug is disclosed. It includes an earplug body having successive and larger rubber hemispheres mounting a valve body to the ear. The valve body defines an aperture centrally of the plug body and central to the ear canal. A slide acts as an acoustical valve seat and selectively opens and closes the valve body. This slide is linear in motion; its size and excursion is dependent upon the physiology of the ear. It brings a sound-transmitting aperture in the slide into and out of registry to permit sounds to directly reach the ear.

SUMMARY OF THE INVENTION

An earplug has a rotationally adjustable gating mechanism for adjustable attenuation of treble sounds. The plug includes a conventional earplug foam body for conforming to and wedging in the ear canal. This earplug foam body includes at least a partial aperture axially of the plug leading from the exterior of the ear canal toward the interior of the ear canal with its hearing sense. A two-part counter rotating gating member fits to the aperture of the earplug. One part of the two part counter rotating gating member has a conical through aperture concentric to the earplug and ear canal. This conical through aperture is partially obstructed by an eccentrically mounted gate. The remaining part of the two part counter rotating gating member defines a rotating cover over the conical aperture and defines at least one and preferably a plurality of sound apertures enabling sound to pass from the exterior of the earplug into the conical aperture. These sound apertures are eccentrically mounted with respect to the conical aperture and the relative rotation to come into and out of registry with the eccentrically mounted gate. The two-part counter rotating gating member has an interference fit into the aperture of the earplug. When the earplug foam body is wedged into the ear, upon relative rotation of the cover with respect to the seat, the sound apertures rotate into and out of registry with the gate. There results an earplug assembly, which can selectively attenuate the treble sounds causing ear discomfort An advantage of this earplug is that simple rotation of one part of the earplug relative to the ear adjustably controls the sound transmission to the eardrum. No external reference—such as the positioning of the slide—is required.

A surprising result is that although the sound admitting apertures are eccentrically mounted, they do not cause any appreciably noticed distortion of sound.

DESCRIPTION OF THE SPECIFIC EMBODIMENTS

Figure 1:
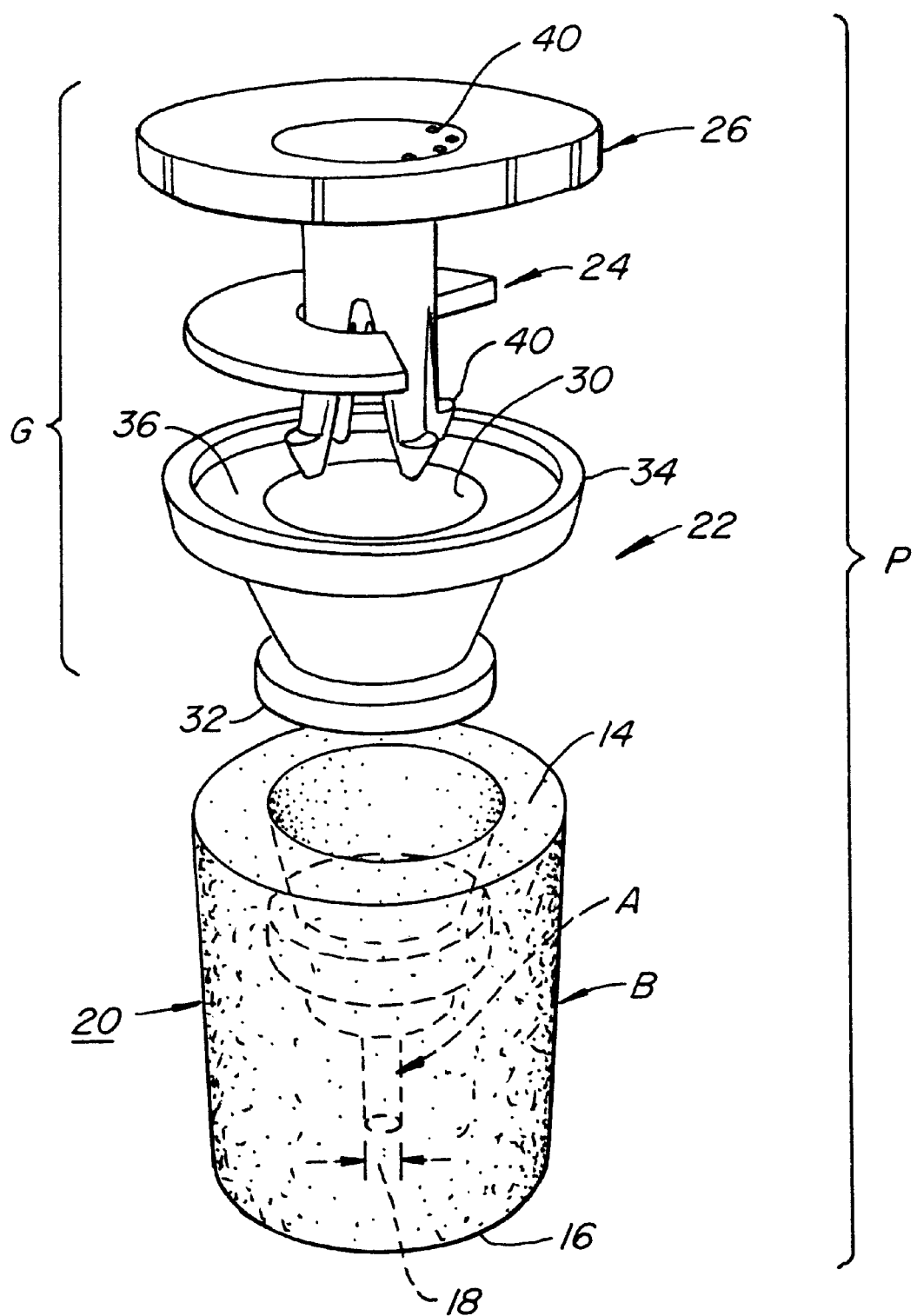
FIG. 1 is an exploded view of the earplug assembly of this invention.

Referring to FIG. 1, conventional earplug foam body B is illustrated. It includes at least a partial aperture A extending from exterior 14 to and toward interior 16 of earplug foam body B. Partial aperture A is here shown having the profile of conical gating member G.

In the normal case, the at least partial aperture A is configured to only have the diameter 18 of the lower part of earplug foam body B. When conical gating member G has a force fit into partial aperture A, earplug foam body B at the portion of the force fit takes on the profile illustrated.

It will be understood that earplug exterior surface 20 conforms to the local physiology of the ear, forming the traditional "snug" fit to the ear canal.

Conical gating member G includes lower concentric conical member 22, eccentric gate 24 which gate forms the top surface of lower concentric conical member 22, and finally relatively rotating sound aperture plate 26.

The construction of lower concentric conical member 22 is easy to understand. It includes conical through aperture 30 with lower rim 32. It is the function of lower rim 32 to key to partial aperture A of earplug foam body B.

There is also provided upper rim 34. Upper rim 34 functions to provide a sliding surface for relatively rotating sound aperture plate 26. It also defines interior of lower concentric conical member 22 annulus 36. Eccentric gate 24 is mounted to annulus 36 and extends beyond annulus 36. This extension partially obstructs conical through aperture 30. As will hereafter appear, sound apertures 40 rotate into and out of registry with eccentric gate 24. This selectively attenuates sound in accordance with user provided relative rotation between relatively rotating sound aperture plate 26 on one hand and lower concentric conical member 22 and eccentric gate 24 on the other hand.

Eccentric gate 24 has a profile, which is normally more than half but less than a third of the 360□ of conical through aperture 30. It is fixed with respect to annulus 36 of lower concentric conical member 22.

Relatively rotating sound aperture plate 26 is also easy to understand. It includes four lower tangs 40 with outwardly facing grasping surfaces 42. As is plainly understandable, when relatively rotating sound aperture plate 26 is pushed downward and on lower concentric conical member 22, sound apertures 40 at outwardly facing grasping surfaces 42 contact lower rim 32. Relatively rotating sound aperture plate 26 is held in firm engagement with lower concentric conical member 22 and eccentric gate 24.

Figure 2:
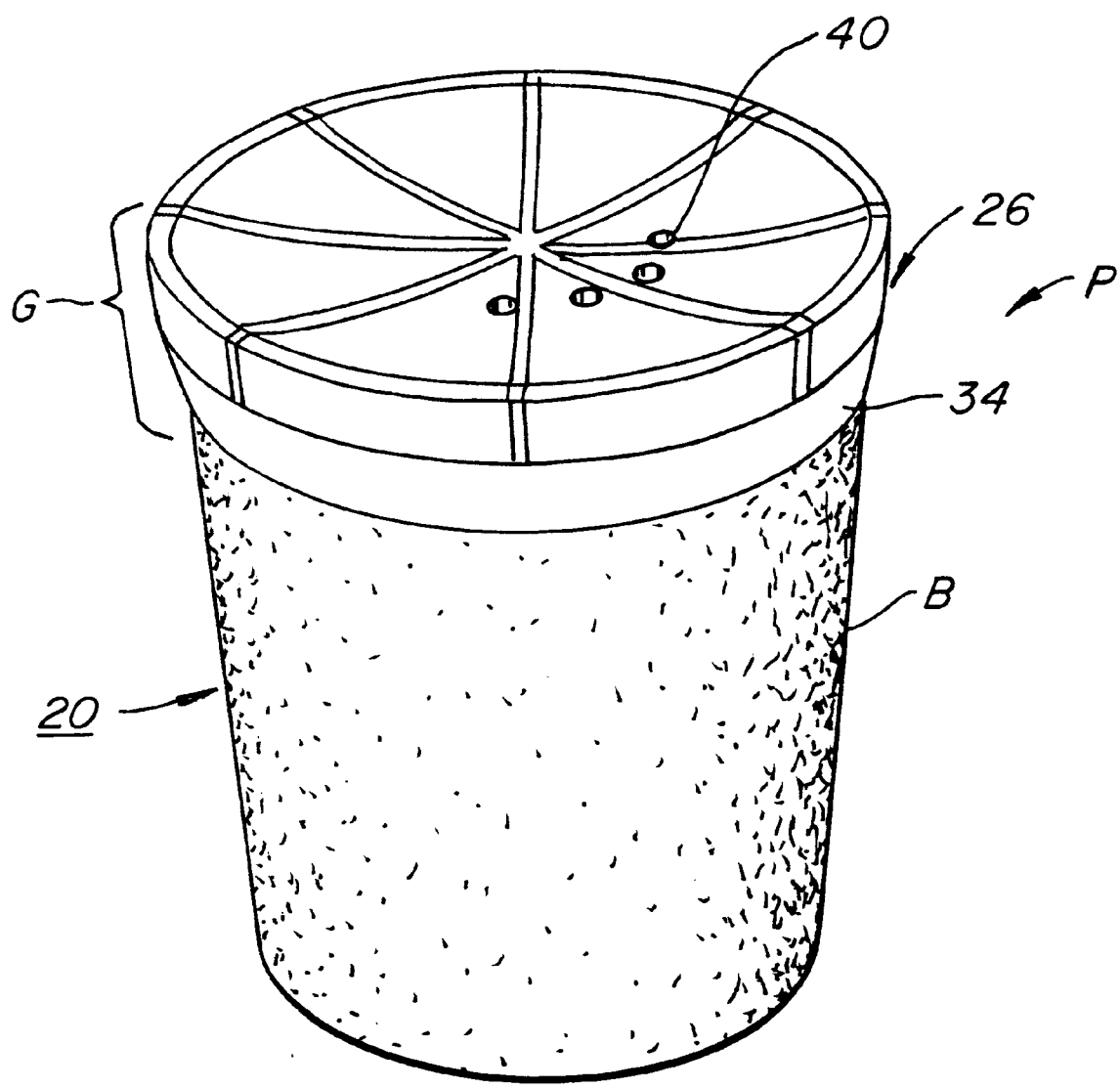
FIG. 2 illustrates the assembled unit illustrating relative rotation to bring one acoustical aperture into registry with the gate and a second acoustical aperture into eccentric registry with the conical aperture of the valve seat to produce the adjustable attenuation of treble sound; and, FIG. 3A, 3B, and 3C are different embodiments of the eccentrically mounted sound admitting apertures illustrating respectively one sound admitting aperture, a plurality of sound admitting apertures all the same size, and a plurality of sound admitting apertures gradually increasing in size.

Presuming that earplug P is assembled as illustrated in FIG. 2, operation is easy to understand. Specifically, relatively rotating sound aperture plate 26 is relatively rotated—preferably by the finger—until sound apertures 40 move into and out of registry with eccentric gate 24. The user of earplug P just listens and turns. No exterior reference of slider position, detent mechanisms or any other reference is required. Relative rotation is continued until treble sound is at its desired amplitude.

Figure 3A:
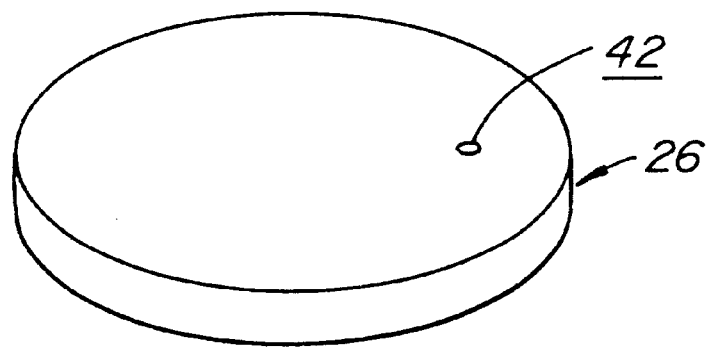
Figure 3B:
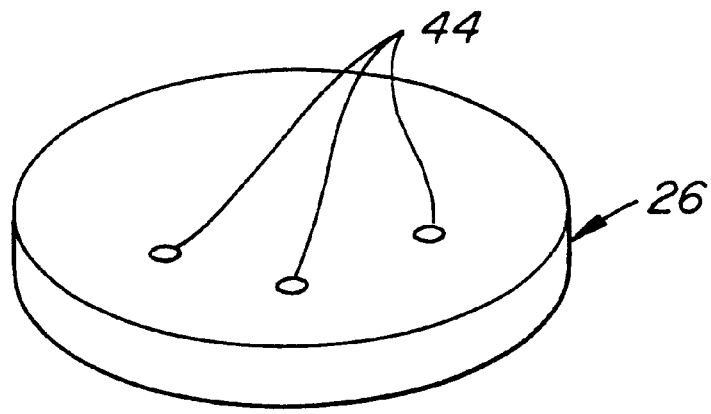
Figure 3C:
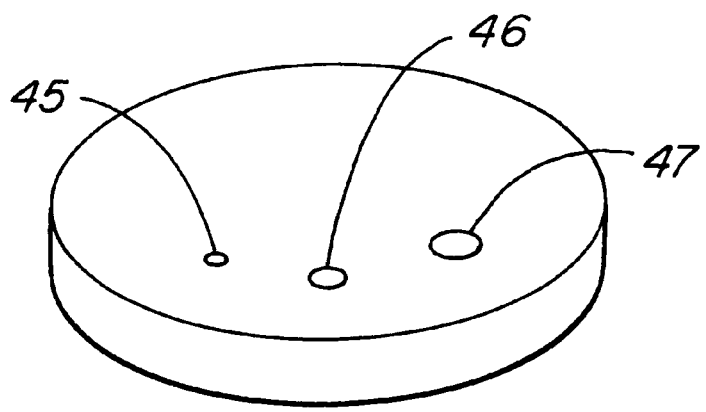

It will be understood that relatively rotating sound aperture plate 26 can contain any number and size of sound apertures 40. Referring to FIG. 3A, single sound aperture 42 appears in relatively rotating sound aperture plate 26. At FIG. 3B, three sound apertures 44 appear, these respective sound apertures all being the same size. Finally, in FIG. 3C, respective sound apertures include small aperture 45, medium aperture 46, and finally large aperture 47.

Some remarks can be generally made about the construction of earplug P. First, sound apertures 40 are all eccentric to conical through aperture 30. This does not interfere with the acoustics of earplug P.

Second, adjustment of earplug P does not require any kind of an external reference. Mere relative rotation of relatively rotating sound aperture plate 26 relative to eccentric gate 24 and lower concentric conical member 22 is all that is required for adjustment. The listener merely removes is finger used for the rotation and listens for the desired level of sound.

Finally, assembly is extraordinarily simple. All parts, earplug foam body B, lower concentric conical member 22, eccentric gate 24, and relatively rotating sound aperture plate 26 can merely be pushed into assembly.

What is claimed is:

1. An adjustable earplug for fitting from the exterior of the body to an ear canal of a listener comprising in combination:
    a foam earplug body having a cylindrical exterior for conforming to an interior of the ear canal, the foam earplug body forming at least a partial aperture axially of the foam earplug body extending from the exterior of the body to and toward the ear canal;
    a valve seat fastened to the aperture of the foam earplug body and defining a central through aperture concentric to the aperture of the foam earplug body;
    an eccentric gate affixed to the valve seat;
    a gating member for concentric rotation on the valve seat and eccentric gating member; and,
    at least one sound aperture defined through the gating member for rotating into and out of registry with the eccentric gating member and the through aperture of the valve seat to selectively attenuate treble sounds passing from the exterior of the body through the adjustable earplug lodged in the ear canal.

2. The adjustable earplug according to claim 1 and wherein:
    a plurality of sound apertures defined through the gating members, each sound aperture for rotating into and out of registry with the gating member.

3. The adjustable earplug according to claim 2 and wherein:
    the plurality of sound apertures includes a first larger sound aperture and a second smaller sound aperture.

4. The adjustable earplug according to claim 2 and wherein:
    the plurality of sound apertures includes apertures of the same size.

5. The adjustable earplug according to claim 1 and wherein:
    the gating member defines a plurality of tangs;
    the plurality of tangs for engagement with the bottom of the through aperture of the central valve seat to maintain the central valve seat in rotational registry with gating member.

6. A process of providing attenuation of treble sounds to an ear canal of a listener in a high noise environment comprising the steps of:
    providing a foam earplug body having a cylindrical exterior for conforming to an interior of the ear canal, the foam earplug body forming at least a partial aperture axially of the foam earplug body extending from the exterior of the body to and toward the ear canal;
    providing a valve seat fastened to the aperture of the foam earplug body and defining a central through aperture concentric to the aperture of the foam earplug body;
    providing an eccentric gate affixed to the valve seat;
    providing a gating member for concentric rotation on the valve seat and eccentric gating member; and,
    providing at least one sound aperture defined through the gating member for rotating into and out of registry with the eccentric gating member and the through aperture of the valve seat to selectively attenuate treble sounds passing from the exterior of the body through the adjustable earplug lodged in the ear canal; and,
    relatively rotating the gating member relative to the valve seat and eccentric gate to bring the at least one sound aperture into and out of registry with the eccentric gate to selectively attenuate treble sound passing to the ear.

* * * * *